(12) United States Patent
Menassa

(10) Patent No.: US 9,662,460 B2
(45) Date of Patent: May 30, 2017

(54) SAFETY SYRINGE FOR NEEDLELESS INJECTOR

(76) Inventor: Karim Menassa, Montreal (CA)

(*) Notice: Subject to any disclaimer, the term of this patent is extended or adjusted under 35 U.S.C. 154(b) by 521 days.

(21) Appl. No.: 13/261,754
(22) PCT Filed: Apr. 3, 2012
(86) PCT No.: PCT/CA2012/000332
§ 371 (c)(1),
(2), (4) Date: Oct. 1, 2013
(87) PCT Pub. No.: WO2012/135943
PCT Pub. Date: Oct. 11, 2012

(65) Prior Publication Data
US 2014/0018731 A1 Jan. 16, 2014

Related U.S. Application Data
(60) Provisional application No. 61/457,460, filed on Apr. 4, 2011.

(51) Int. Cl.
A61M 5/50 (2006.01)
A61M 5/30 (2006.01)
A61M 5/24 (2006.01)
(52) U.S. Cl.
CPC ............. A61M 5/504 (2013.01); A61M 5/30 (2013.01); A61M 5/24 (2013.01); A61M 2005/2488 (2013.01); A61M 2005/5046 (2013.01); A61M 2005/5073 (2013.01)

(58) Field of Classification Search
CPC ............... A61M 5/504; A61M 5/5066; A61M 2005/5046; A61M 5/30; A61M 2005/5073; A61M 5/5013
See application file for complete search history.

(56) References Cited

U.S. PATENT DOCUMENTS

| 4,950,251 | A | * | 8/1990 | Haining | A61M 5/322 604/110 |
| 5,064,413 | A | * | 11/1991 | McKinnon | A61M 5/30 604/143 |
| 5,643,211 | A | * | 7/1997 | Sadowski | A61M 5/30 604/110 |
| 6,063,054 | A | * | 5/2000 | Anderson | A61M 5/30 604/70 |
| 6,267,749 | B1 | * | 7/2001 | Miklos | A61M 5/5013 604/110 |
| 7,744,563 | B2 | * | 6/2010 | Landau | A61M 5/2053 604/68 |
| 2005/0054979 | A1 | * | 3/2005 | Liu | A61M 5/3243 604/110 |

* cited by examiner

Primary Examiner — Theodore Stigell
Assistant Examiner — Benjamin Koo
(74) Attorney, Agent, or Firm — George A. Seaby

(57) ABSTRACT

A disposable syringe for use in a needleless injector includes a tubular body with an open rear end, a closed front end containing an injection orifice, a chamber in the body for receiving a liquid and a plunger slidable in the chamber for pushing the liquid out of the orifice. A tip is provided on the inner end of the plunger for separation from the remainder of the plunger to block the orifice when the plunger is retracted after an injection, whereby the syringe cannot be re-used.

4 Claims, 11 Drawing Sheets

SAFETY SYRINGE FOR NEEDLELESS INJECTOR

CROSS-REFERENCES TO RELATED APPLICATIONS

This application is a 35 USC §371 application of International Application PCT/CA2012/000332 filed Apr. 3, 2012, which claims priority to provisional application U.S. 61/457,460, filed Apr. 4, 2011.

BACKGROUND OF THE INVENTION

This invention relates to a disposable syringe, and in particular to a disposable syringe for single use in a needleless injector.

U.S. Pat. No. 5,190,523 issued to I. Lindemayer on Mar. 3, 1990 discloses a disposable syringe and a needleless injector. There are many other patents and published patent applications relating to needleless injectors, including U.S. Pat. No. 7,357,915, issued to K. Menassa on Apr. 15, 2008. In spite of the large amount of activity in the field, there still exists a need for a safety syringe for a needleless injector which can be used once and only once. The present invention is believed to meet such need.

SUMMARY OF THE INVENTION

Accordingly, the invention provides a disposable syringe for a needleless injector which includes a tubular body defining a fluid chamber, i.e. a chamber for receiving a fluid such as a medicine, the body having an open end for slidably receiving a piston and a closed end; a coupler for connecting the body to the discharge end of an injector barrel, an orifice in said closed end of the body for discharging fluid from the chamber when the piston is pushed towards the orifice, a separable tip on an end of the piston in the body, whereby, when the piston is pushed fully into the body to eject fluid therefrom, the tip separates from the piston and remains in the body in an orifice sealing position, preventing re-use of the syringe.

BRIEF DESCRIPTION OF THE DRAWINGS

The invention is described below in greater detail with reference to the accompanying drawings, wherein.

DETAILED DESCRIPTION OF THE DRAWINGS

Figure 1:
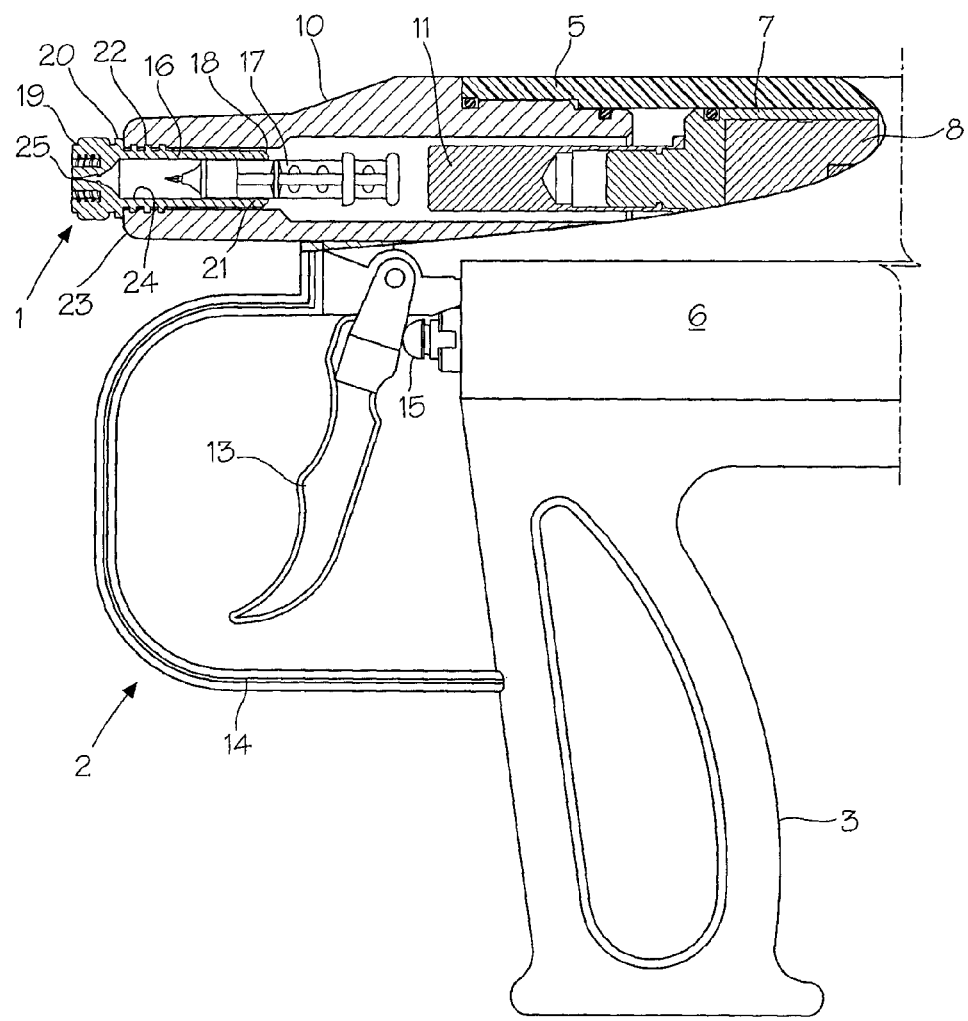
FIG. 1 is a partly sectioned side view of one end of a pistol-type needleless injector containing a disposable syringe in accordance with the invention.

Referring to FIG. 1, a syringe in accordance with the present invention which is indicated generally at 1 is intended for use in a needleless injector 2, which in this case is in the shape of a pistol. The injector 2 includes a body with a handle 3 extending downwardly from approximately the center thereof. The body is defined by upper and lower cylinders 5 and 6, respectively, which contain most of the remaining elements of the injector. For the most part, the elements of the injector 2 are the same as or similar to the elements of the injector described in above-mentioned U.S. Pat. No. 7,357,915.

A brass piston 7 is slidably mounted in the cylinder 5. The piston 7 is generally cup-shaped, including a rear recess for receiving a cylindrical, permanent magnet 8. A tubular barrel 10 is connected to the front end of the cylinder 5. The piston 7 is used to drive a plunger 11 mounted on the front end of the piston 7. Movement of the piston 7 and the plunger 11 are controlled by a trigger 13, which is protected by a trigger guard 14, and a plunger 15 extending out of the cylinder 6 for controlling a valve (not shown) in the cylinder 6. The valve is similar to that disclosed by the above-referenced U.S. Pat. No. 7,357,915. Forward movement of the plunger 11 in the barrel 10 causes operation of the syringe 1.

Figure 2:
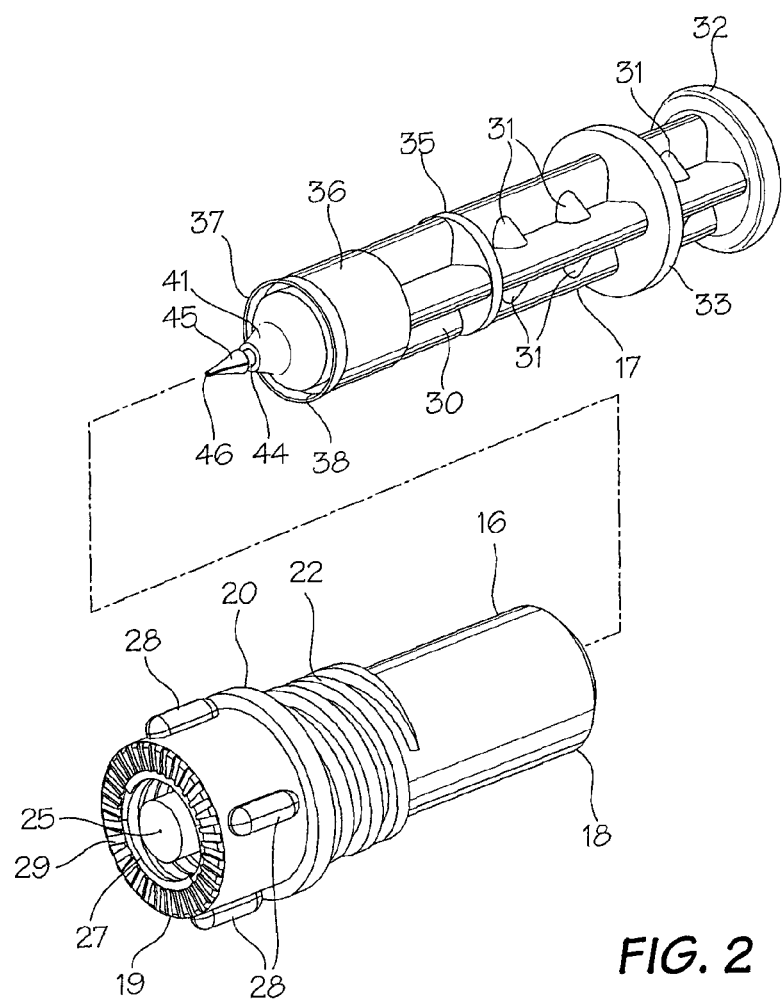
FIG. 2 is an exploded, isometric view of the disposable syringe of FIG. 1.
Figure 3:
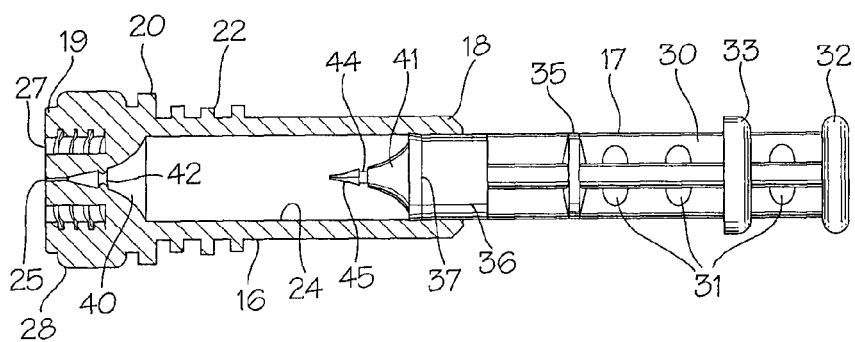
FIG. 3 is a longitudinal sectional view of the syringe of FIGS. 1 and 2.
Figure 4:
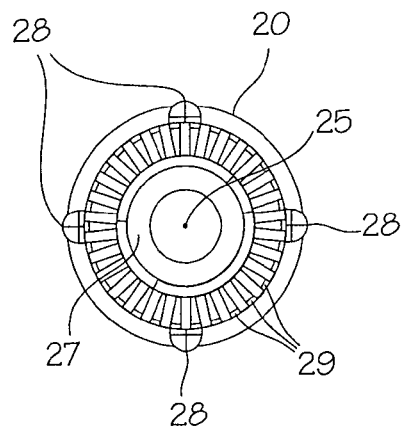
FIG. 4 is a front view of the syringe of FIGS. 1 to 3.

As best shown in FIGS. 2 and 3, the syringe 1 includes a tubular body 16 for slidably receiving a piston or plunger 17. The body 16 has an open inner end 18 (when mounted in the barrel 10 of the injector) and a closed outer end 19. An annular flange 20 near the outer end 19 limits movement of the body 16 into the barrel 10. Threads 22 on the body 16 behind the flange 20 engage the internally threaded discharge end 23 of the injector barrel 10 when mounting the syringe in the injector. Fluid, typically medicine, from a chamber 24 in the body 16 is discharged through an orifice 25 in the outer end 19 of the body 16. An externally threaded recess 27 in the end 19 forms part of a luer lock for connecting a conventional externally threaded needle, catheter or other device (not shown) to the syringe. Longitudinally extending ribs 28 on the cylindrical outer end 19 of the body 16 facilitate gripping of the body when screwing the syringe into the injector barrel 10. Radially extending teeth 29 on the annular periphery of the closed end 19 of the body 16 prevent rotation of the body when the injector is in use, i.e. when the orifice 25 or the outer end 19 of the body 16 is pressed against the skin during an injection.

In one embodiment, the plunger 17 includes an elongated body 30 of cruciform cross section throughout most of its length with reinforcing gussets 31. A pair of spaced apart discs 32 and 33 are provided at and near the inner end of the body 30. The disc 32 is engaged by the plunger 11 during an injection. The disc 33 slides into the narrow discharge end of the barrel 10 during injection and limits movement of the plunger 17 into the body 16 of the syringe. A third disc-shaped reinforcing rib 35 is provided roughly halfway between the rib 33 and the cylindrical outer end 36 of the plunger body 30. A skirt 37 flares outwardly from an annular recess 38 (FIG. 2) in the outer end of the body 30 for sealing engagement with the passage 24.

Figure 5:
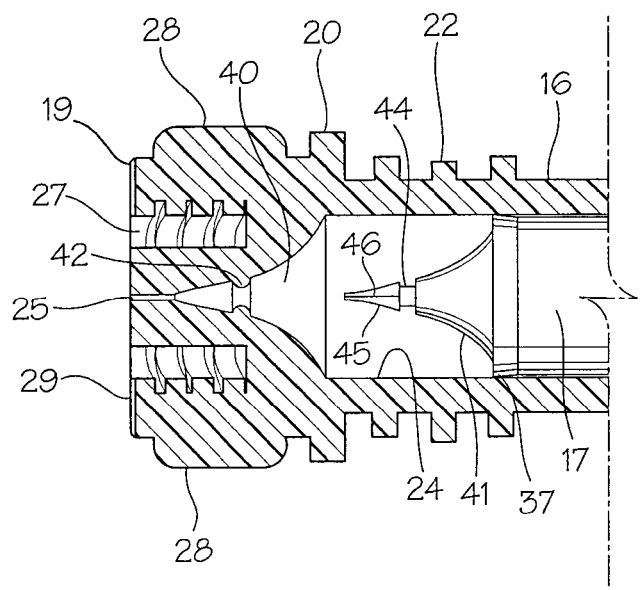
FIG. 5 is a longitudinal sectional view of one end of the syringe of FIGS. 1 to 4.

As best shown in FIG. 5, the discharge end 40 of the chamber 24 and the corresponding end 41 of the plunger 17 have essentially the same shape. The end 40 of the passage 24 tapers to the orifice 25 and includes an annular projection or restriction 42. The end 41 of the plunger 17 has a taper identical to that of the end 40 of the passage 24, and an annular groove 44 (line of weakness) near the tip 45 thereof. A longitudinally extending slot 46 is provided in the tip 45 so that the tip can compress when encountering the restriction 42.

Figure 6:
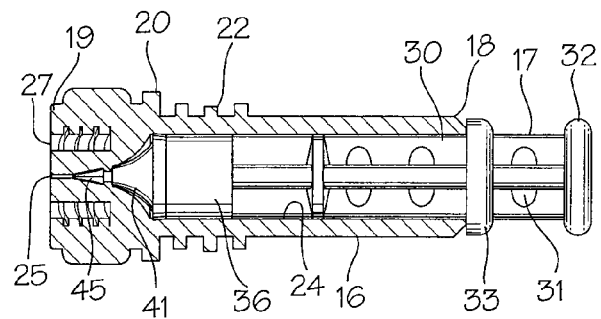
FIGS. 6 and 7 are longitudinal sectional views showing the operation of hte syringe of FIGS. 1 to 4.
Figure 7:
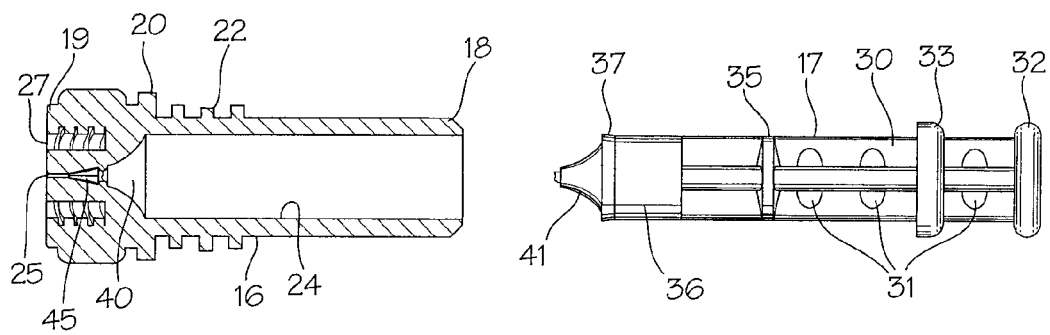

In operation, the orifice end of the syringe is connected to a medicine bottle (not shown) and the plunger 17 is retracted to draw medicine into the passage 24. When the plunger 17 is pushed into the body 16 (FIG. 6), the tip 45 is jammed into the end 40 of the passage 24, and the projection 42 enters the groove 44. When the plunger 17 is retracted (FIG. 7), the narrow tip 45 of the plunger remains in position against the orifice 25 while the remainder of the plunger is retracted. Thus, the orifice 25 is permanently blocked from the inside, prevent re-use of the syringe.

Figure 8:
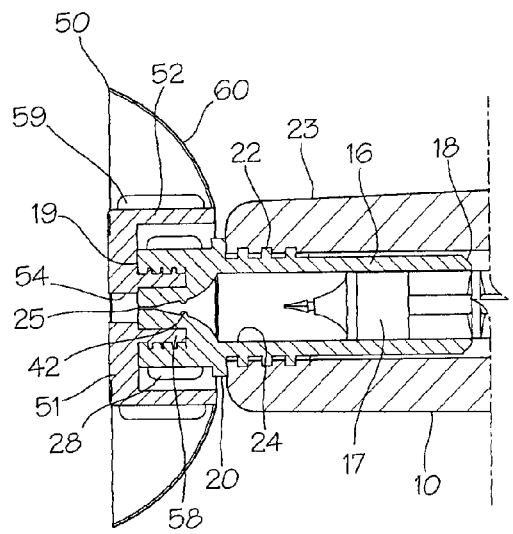
FIG. 8 is a longitudinal sectional view of the syringe of FIGS. 1 to 4 with a guard.

As shown in FIG. 8, a guard 50 can be mounted on the end 19 of the syringe body 16. The guard 50 performs a dual function, viz it prevents spray from the injection site, and spaces the orifice 25 from the injection site. For such purpose, the guard 50 is shaped like a cap with a circular outer end 51 and a cylindrical side wall 52. A central hole 54 in the end 51 permits passage of fluid from the orifice 25 to an injection site. Because the orifice 25 is spaced from the injection site by the thickness of the end 51, the force of the fluid is less than if the orifice 25 was pressed against the injection site. Thus, the guard 50 is used when making subcutaneous injections. An externally threaded sleeve 58 integral with the end 51 mates with the threaded recess 27 in the end 19 of the body 16 to connect the guard 50 to the syringe. Projections or ribs 59 are gripped when screwing the syringe into the barrel 10 of the injector. A thin, cup-shaped shield 60 extends outwardly from the rear end of the side wall 52 for surrounding an injection site.

Figure 9:
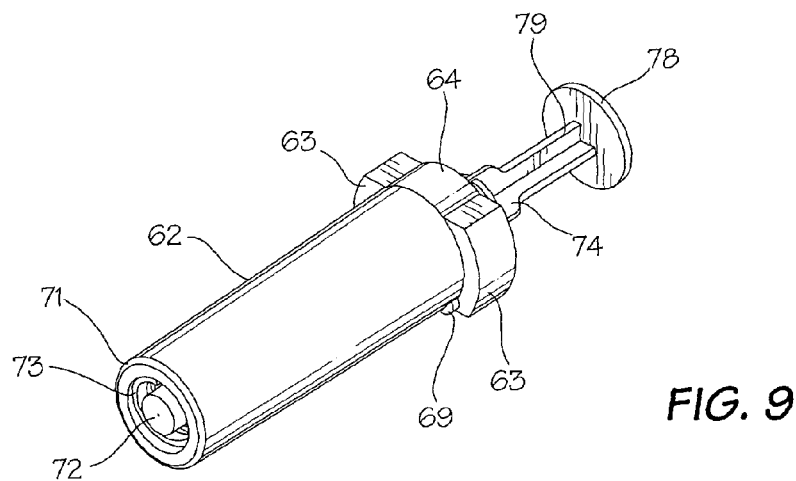
FIG. 9 is an isometric view of a second embodiment of the syringe.
Figure 10:
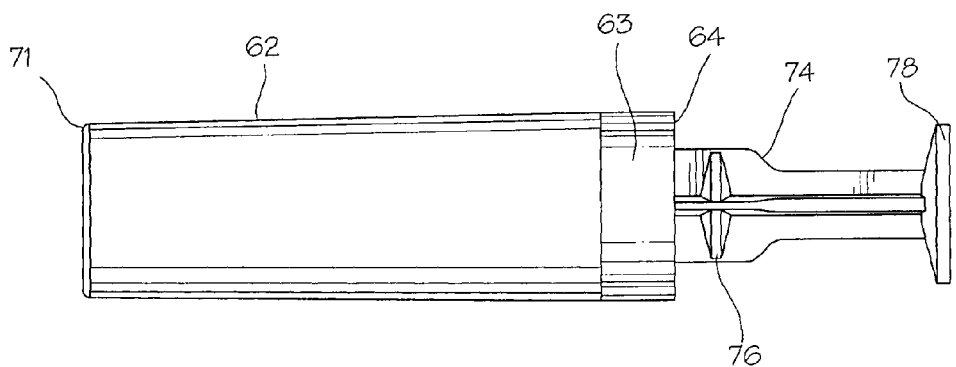
FIG. 10 is a side view of the syringe of FIG. 9.
Figure 11:
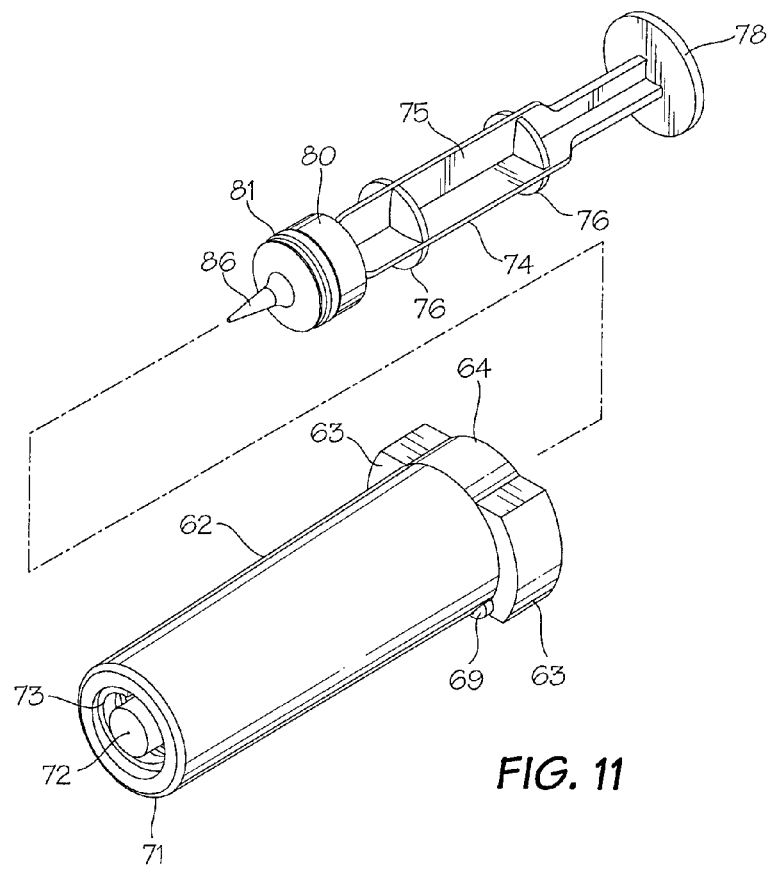
FIG. 11 is an exploded isometric view of the syringe of FIGS. 9 and 10.
Figure 12:
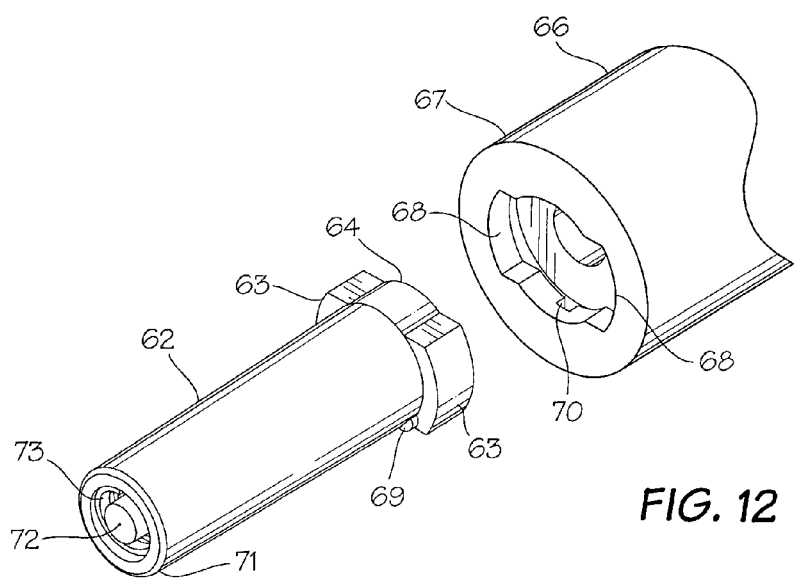
FIG. 12 is an isometric view of one end of an injector barrel and the syringe of FIGS. 9 to 11 with parts omitted.

Referring to FIGS. 9 to 11, a second embodiment of the invention includes a tubular body 62 with a pair of arcuate ears 63 at the inner end 64 thereof. The ears 63 are used in a bayonet coupling for mounting the syringe in the end of an injector barrel 66, one end 67 of which is shown in FIG. 12. The interior of the open end 67 of the barrel 66 includes a pair of opposed recesses 68 for receiving the ears 63. The ears 63 pass through the recesses 68, and then the body 62 is rotated to releasably lock the syringe in the barrel 66. When the body 62 is rotated to the locked position, a small projection 69 on the outer end of one ear 63 enters a notch 70 in the end of the barrel 66. As in the first embodiment of the invention, the outer end 71 of the body 62 contains an orifice 72 and a threaded recess 73 for use in a luer connector.

A plunger 74 is slidably mounted in the body 62. The plunger 74 includes an elongated body 75 of cruciform cross section reinforced by disc-shaped ribs 76. A large disc 78 on the inner end 79 of the body 75 supports the body for sliding in the injector barrel 66. The cylindrical outer end 80 of the plunger body 75 contains a groove 81, carrying an O-ring 82 (FIGS. 13 to 15) for sealing the plunger 74 in the body 62 of the syringe.

Figure 13:
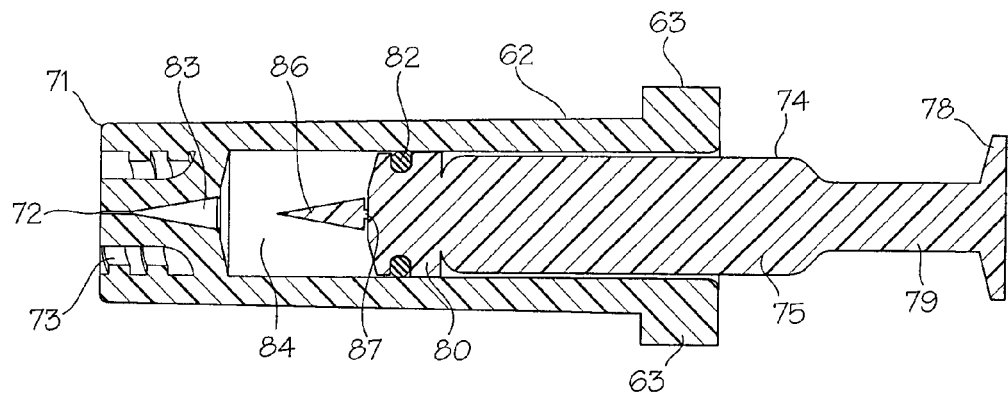
FIGS. 13 to 15 are longitudinal sectional views showing the operation of the syringe of FIGS. 9 to 11.
Figure 14:
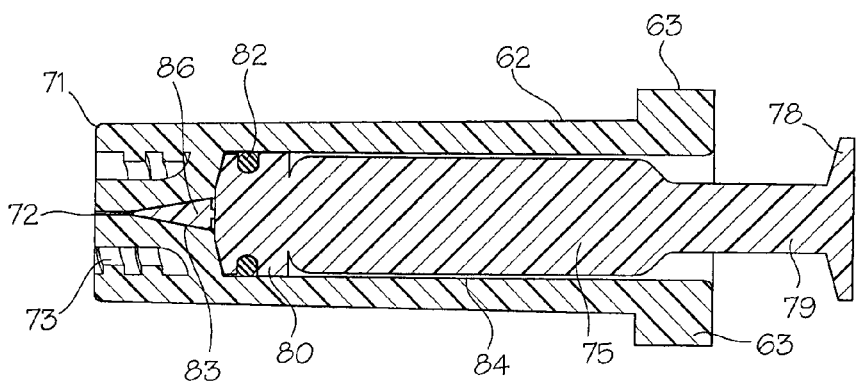
Figure 15:
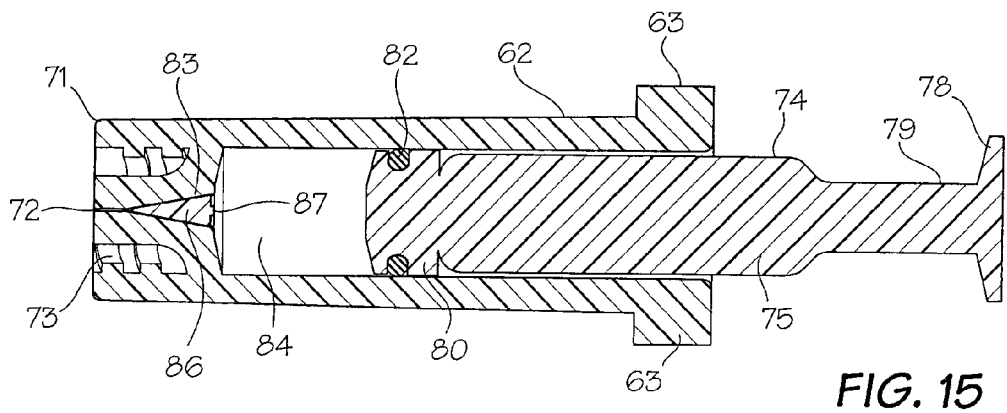

The discharge end 83 of a chamber 84 in the syringe body 62 is conical. As illustrated in FIGS. 13 to 15, when the plunger 74 is moved from a retracted position (FIG. 13) to the extended, injection position (FIG. 14), a conical head 86 on the outer end 80 of the plunger is jammed into the conical discharge end 83 of the chamber 84. Because the head 86 is connected to the remainder of the plunger body 75 by a very narrow, frangible neck 87, when the plunger 74 is retracted, the head 86 remains in the conical discharge end 83 of the chamber 84. Thus, the orifice 72 is sealed, preventing re-use of the syringe. In order to ensure separation of the head 86, the diameters of the conical discharge end 83 of the chamber 84 and the head 86 must be such that the head is retained in the passage by friction, i.e. they must be the same size or the head can be slightly larger in diameter than the passage.

Figure 16:
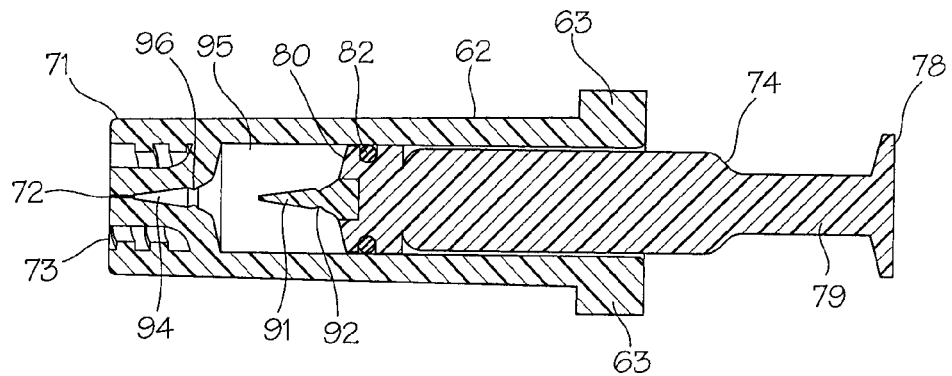
FIGS. 16 to 18 are longitudinal sectional views of a third embodiment of the syringe.
Figure 17:
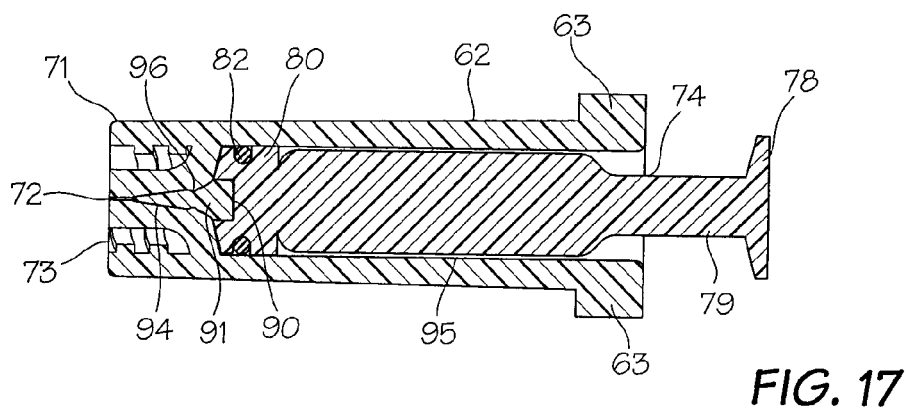
Figure 18:
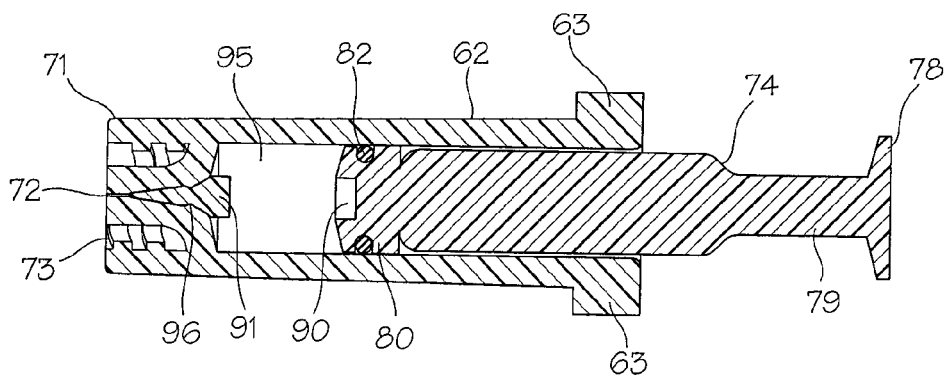

In a third embodiment of the invention (FIGS. 16 to 18) the outer end 80 of the plunger 74 includes a cylindrical recess 90 holding the cylindrical inner end of a generally conical head 91. The head 91 contains an annular groove 92 (FIG. 16) and the generally conical discharge end 94 of the chamber 95 contains an annular projection 96. As in the case of the head 86 in the second embodiment of the invention (FIGS. 13 to 15), when the plunger 74 is extended (FIG. 17), the head 91 is jammed into the end 94 of the chamber 95. The projection 96 mates with the recess 92 in the head 91. Thus, when the plunger 74 is retracted (FIG. 18), the head 91 remains in the discharge end 94 of the chamber 95 is blocking the orifice 72.

Figure 19:
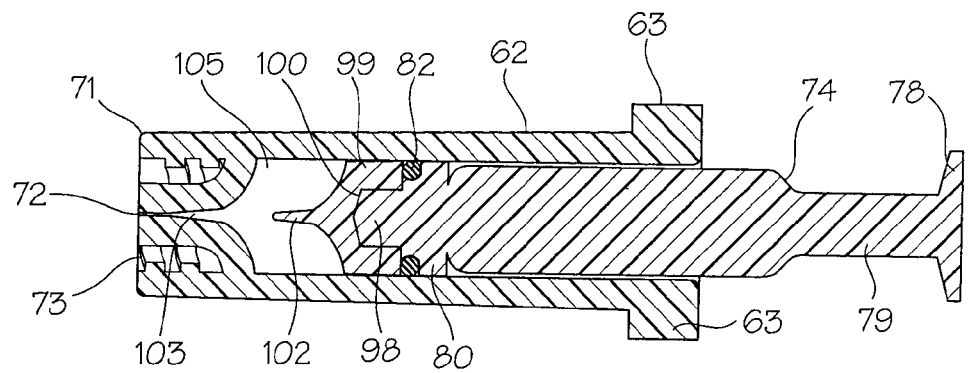
FIGS. 19 to 21 are longitudinal sectional views of a fourth embodiment of the syringe of the present invention.
Figure 20:
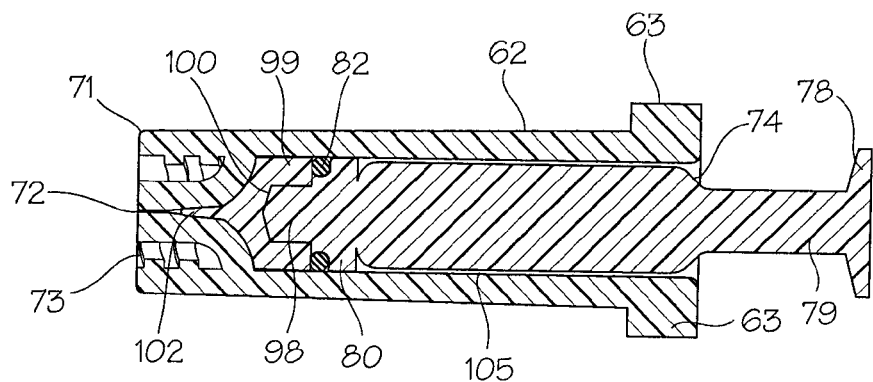
Figure 21:
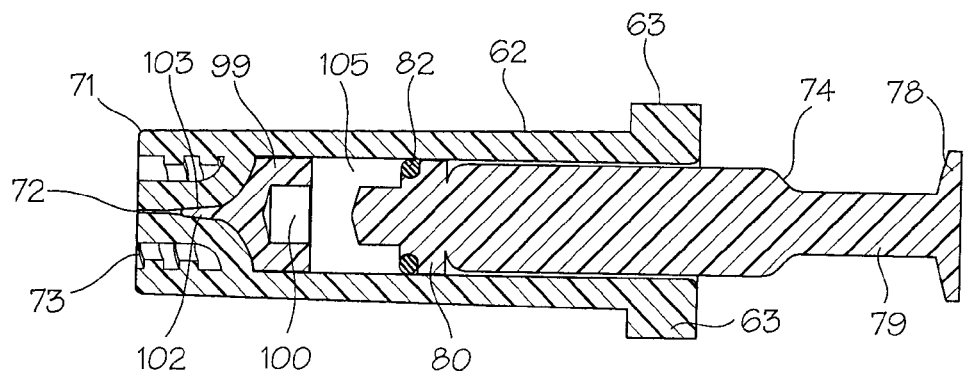

With reference to FIGS. 19 to 21, in a fourth embodiment of the invention, the outer end 80 of the plunger 74 includes a narrow diameter, cylindrical projection 98 carrying a head 99, which is separable from the end 80. For such purpose, the head 99 includes a recess 100 in the inner end thereof. During an injection, the conical tip 102 of the head 99 is jammed into the conical discharge end 103 of the medicine chamber 105 to seal the orifice 72.

FIGS. 22 to 26 illustrate disposable nozzle assemblies in accordance with the invention. The nozzle assemblies of FIGS. 22 to 26 are intended for use on a disposable injector of the type illustrated in U.S. Pat. No. 7,357,915.

Figure 24:
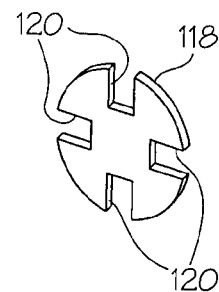
FIG. 24 is an isometric view of a spacer used in the injector of FIGS. 22 and 23.
Figure 25:
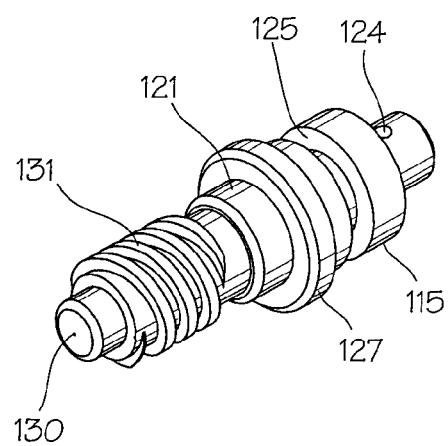
FIG. 25 is an isometric view of the nozzle of FIGS. 22 and 23.

The discharge end 109 of the barrel 110 of the earlier injector includes a piston assembly 111 for forcing liquid through a valve 112 defined by a flexible, hollow valve stem 113 in the inlet end 114 of a nozzle 115, and a flexible rubber valve head 116. A circular stainless steel spacer 118 is sandwiched between the valve head 116 and an annular shoulder 119 in the barrel 110. As best shown in FIG. 24, the spacer 118 includes four diametrically opposed notches 120 or a plurality of such notches in the periphery thereof. The notches 120 permit the flow of liquid around the valve head 116. When the liquid in the barrel 110 is subjected to a sufficiently high pressure, liquid flows through the notches 120 compressing the valve 113, whereby liquid from the barrel 110 flows into the nozzle 115.

The nozzle 115 is defined by a tubular body 121 with a passage 122 therethrough. A pair of diametrically opposed holes 124 in the inner or inlet end of the body 121 are normally closed by the valve stem 113. The body 121 is slidable in the open discharge end of the barrel 110. An annular groove 125 (FIG. 25) in the body 121 receives an O-ring 126 for sealing the nozzle in the barrel 110. An annular flange 127 on the middle of the body 121 is sandwiched between the outlet end of the barrel 110 and an internally threaded cap or nut 128 mounted on the externally threaded outer end 109 of the barrel 110. Liquid is discharged from the nozzle 115 through an orifice 130 in the otherwise closed outer end of the body 121.

The outer end of the body 121 includes external threads 131 for mating with the internally threaded tubular body 134 of a guard 135. Liquid exiting the orifice 130 is discharged through an aligned orifice 136 in the body 134. A generally hemispherical shield 137 extends outwardly from the inner or rear end of the guard body 134.

Figure 22:
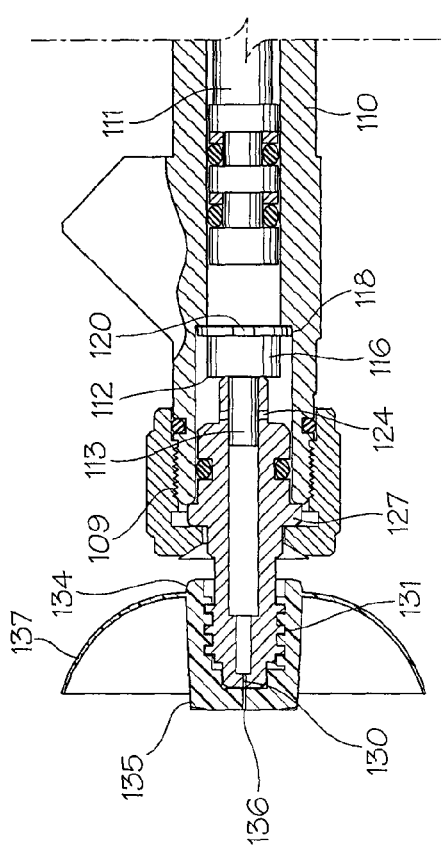
FIG. 22 is a longitudinal sectional view of one end of a needleless injector incorporating a disposable nozzle in accordance with the invention.
Figure 23:
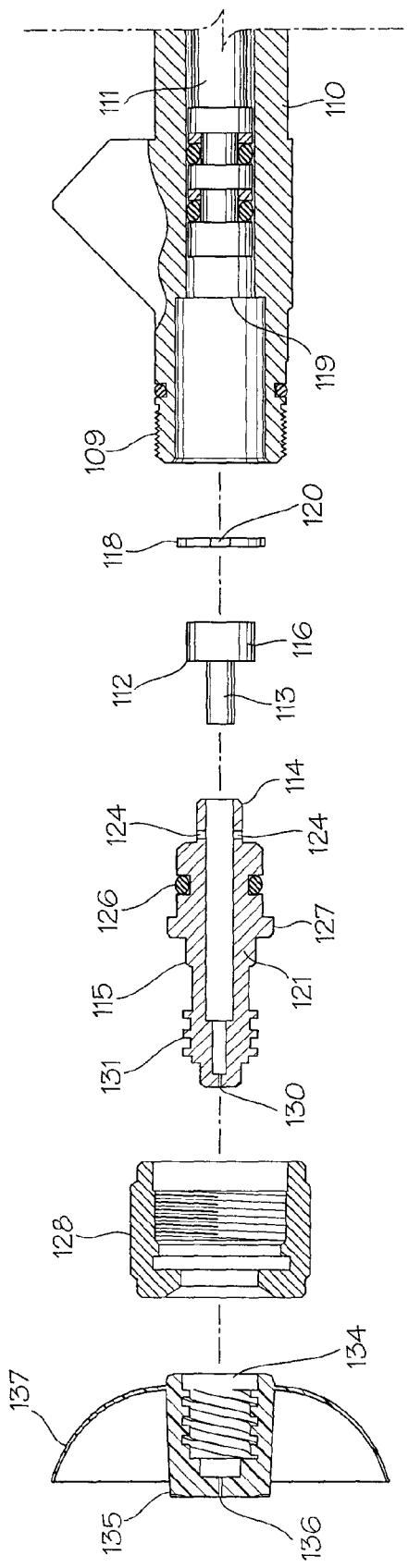
FIG. 23 is an exploded, longitudinal sectional view of the injector and nozzle of the FIG. 22.
Figure 26:
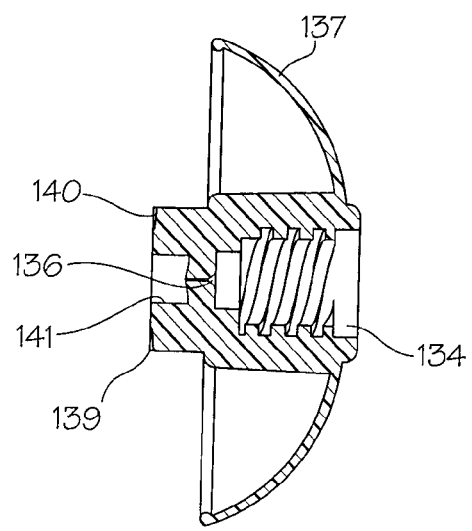
FIG. 26 is a longitudinal sectional view of one end of the nozzle of FIG. 25 and a second embodiment of a guard used thereon.

The guard 139 of FIG. 26 is similar to the guard 135 of FIGS. 22 and 23, except that the outer end 140 of the body 134 is thicker and includes a cylindrical recess 141. Thus, when the outer end 140 is pressed against an injection site (not shown), there is a gap between the orifice 136 and the injection site.

It will be appreciated that with the apparatuses of FIGS. 22 to 26, following an injection, it is only the guard which needs to be replaced.

The invention claimed is:

1. A disposable syringe for use in a needleless injector comprising a tubular body having an open end and a partially closed end, a chamber in said tubular body for receiving a fluid, an orifice in the partially closed end of the tubular body for discharging fluid from the tubular body; said chamber having a conical discharge end behind and in fluid communication with said orifice; an annular projection in said conical discharge end of the chamber; a plunger slidable through said open end of the tubular body into said chamber for causing the discharge of fluid from the tubular body when the plunger is pushed towards the orifice; a conical tip on a conical discharge end of the plunger for plugging said orifice when the plunger is pushed into said chamber, the conical tip of the plunger having the same shape and size as the conical discharge end of the chamber; and an annular groove in said tip of said plunger for mating with said projection, whereby, when the plunger is jammed into the chamber and then retracted, the conical tip of the plunger breaks in the area of said groove and the conical tip is retained in the discharge end of the chamber by the annular projection completely blocking the orifice.

2. The disposable syringe of claim 1, including an annular flange on the partially closed end of the tubular body for limiting movement of the syringe into a needleless injector barrel.

3. The disposable syringe of claim 1, wherein said plunger has a cruciform cross section throughout most of its length.

4. The disposable syringe of claim 1 further comprising a longitudinally extending slot in said conical tip of the plunger permitting compression of the tip when encountering the annular projection in the tubular body.

* * * * *